United States Patent [19]

Kirschner et al.

[11] 4,021,920

[45] May 10, 1977

[54] DRILLING OR MILLING APPARATUS FOR THE WORKING OF LIVE BONE, PARTICULARLY FOR DENTISTRY

[76] Inventors: Horst Kirschner, Wilhelmstrasse 56, D-63 Giessen; Wolfgang Meyer, Heerstrasse 18, D-3569 Erdhausen, both of Germany

[22] Filed: Mar. 13, 1975

[21] Appl. No.: 558,075

Related U.S. Application Data

[63] Continuation-in-part of Ser. No. 478,586, June 12, 1974, abandoned.

[30] Foreign Application Priority Data

June 18, 1973 Germany .......................... 2331023

[52] U.S. Cl. ....................................... 32/28; 32/48
[51] Int. Cl.² ....................................... A61C 1/08
[58] Field of Search ............... 32/27, 28, 59; 72/70, 72/76, 341, 367; 408/59; 279/20

[56] References Cited

UNITED STATES PATENTS

| | | |
|---|---|---|
| 2,400,912 | 5/1946 | Britt et al. ........................... 32/59 |
| 2,738,528 | 3/1956 | Fridge ................................. 32/59 |
| 3,136,059 | 6/1964 | Nelson ................................ 32/28 |
| 3,576,076 | 4/1971 | Weissman ........................... 32/48 |

Primary Examiner—Robert Peshock
Attorney, Agent, or Firm—Woodhams, Blanchard and Flynn

[57] ABSTRACT

Cooling means for bone or tooth cutting tool. In order to cool the cutting surfaces of a bone or tooth cutting tool, there is provided in the supporting shank of the cutting tool a first chamber containing the driving means for the tool and a second chamber within or communicating with the cutting tool itself, said two chambers being separated by a perforable diaphragm seal. Conduit means for introducing cooling media into the interior of said tool is received into a suitable recess in the upper portion of the tool housing, extends through said first chamber and is provided with a pointed tip for piercing said diaphragm seal for extending into said second chamber. Cooling media is then introduced into the interior of said tool and exits therefrom for cooling both the tool itself and the material being cut.

18 Claims, 4 Drawing Figures

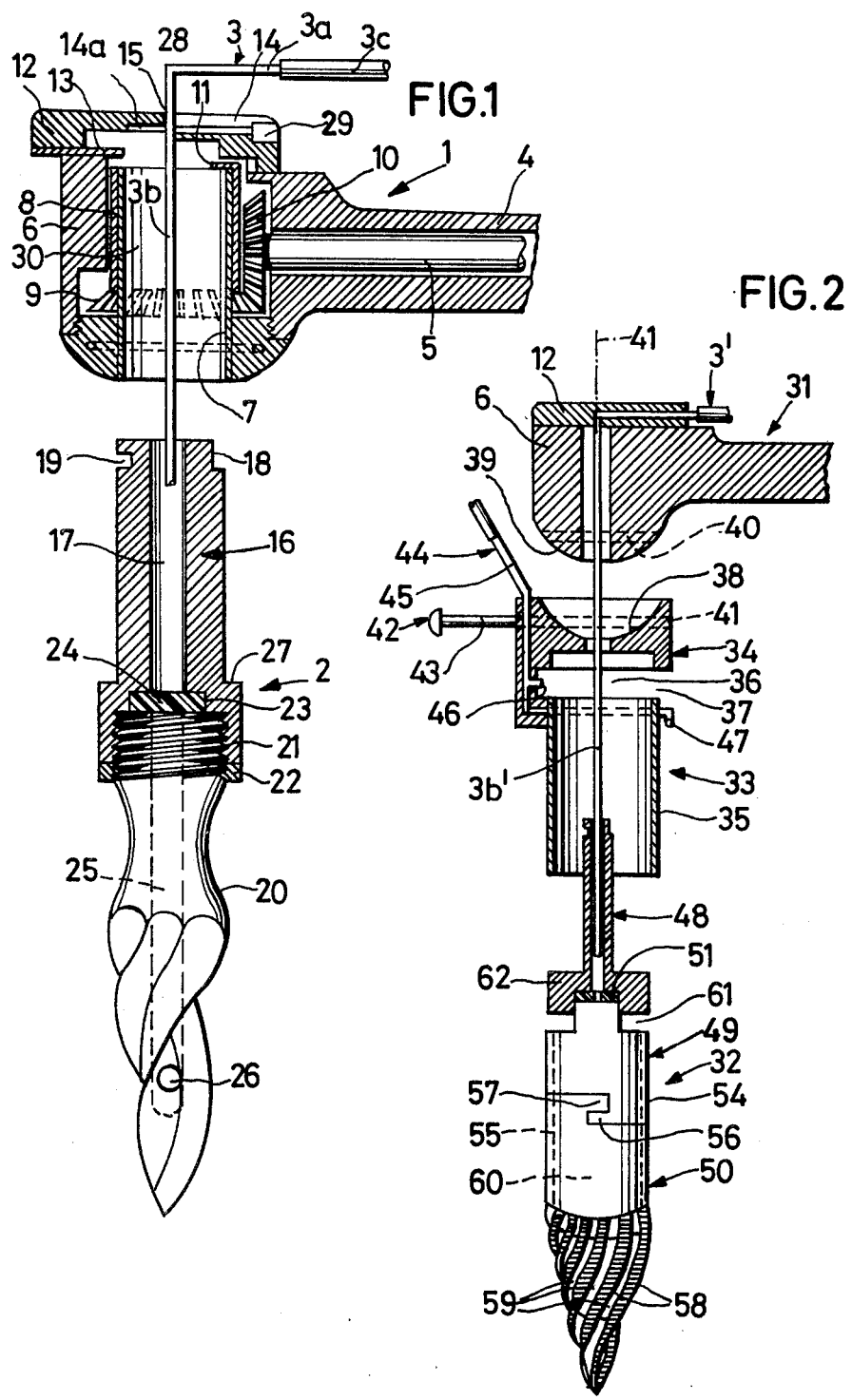

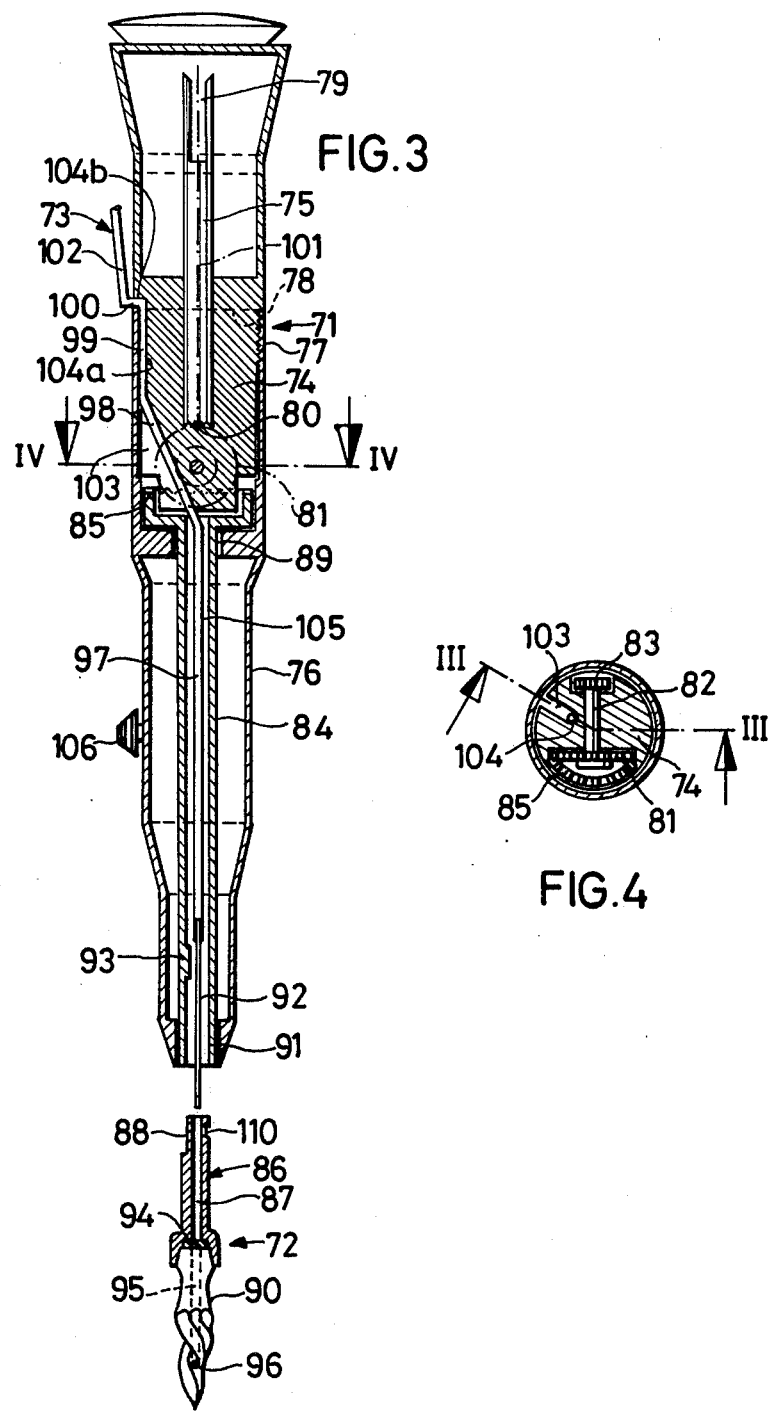

DRILLING OR MILLING APPARATUS FOR THE WORKING OF LIVE BONE, PARTICULARLY FOR DENTISTRY

This application is a continuation-in-part application of our copending application Ser. No. 478,586, filed June 12, 1974, now abandoned.

FIELD OF THE INVENTION

The invention relates to a drilling or milling apparatus for the working of live bone, in particular for dentistry, having a handle in the form of a hand piece or an elbow, in which a drivable shaft is supported, a tool in the form of a drill or milling tool fixedly coupled with the shaft for rotation therewith and a conduit for feeding cooling fluid to the tool. The tool has a longitudinal channel, which at the working end of the tool opens outwardly and the conduit is a stationary small tube, which projects into the longitudinal channel.

BACKGROUND OF THE INVENTION

In human and veterinary medicine, it is often necessary to remove or cut live bone, such as in the drilling of holes into the teeth or jawbone in dentistry, the cutting of jawbone in oral surgery and the cutting of the skull in neurosurgery. It is in such case highly desirable, and in many cases absolutely necessary, for the success of such an operation that the bone be not damaged because otherwise the healing of implants or the knitting of a cut bone is very difficult or even may not be possible.

Further, damage to such bone can be expected at relatively low temperatures. The highest temperature which the tooth or other bony substance will tolerate lies at approximately 50° C.

It is known to dissipate frictional heat by conducting a cooling fluid, such as water of physiological saline solution, as close as possible to the place of heat formation. For this purpose, nozzles for the discharge of cooling fluid are usually arranged on dental hand or elbow pieces, which nozzles spray cooling fluid from outside onto the tool (drill, milling tool). This method achieves a good cooling of the tool, however, it is often not possible to withdraw the heat from the place of formation, namely where the cutting surfaces rub on the substance which is to be removed. This is particularly true if drilling is done in relatively deep holes or if mechanical obstacles prevent the access of the cooling fluid to the tool portion which is in engagement with the substance to be removed. Thus with the known method the heat removal is often only indirectly possible through the tool. However, this type of heat removal is often not sufficient to prevent an intolerable heating of tooth or bony substance because of the poor heat transfer from the substance into the tool.

A disadvantage of the method used so far consists also in that relatively large amounts of cooling media must be supplied in order to obtain an at least somewhat sufficient cooling. The discharge of large amounts of cooling fluid is often difficult, for example, when a tooth treatment is carried out with the patient in a lying position.

The basic purpose of the invention is to improve an apparatus of the type mentioned above in such a manner that cooling fluid can be fed directly to the place of the heat development including when work takes place at a place which is difficult of access, for example in a deep hole.

This purpose is attained according to the invention by providing the tool with a longitudinal channel which opens outwardly at the working end of the tool and causing the conduit to communicate with the longitudinal channel.

During use of apparatus so constructed, the cooling fluid is conducted through the longitudinal channel to the front end of the tool and immediately after its exiting from the tool contacts the substance to be cooled. This is also assured when drilling takes place in a deep hole or if mechanical obstacles exist which would not permit an effective cooling from the outside. The apparatus of the invention, due to the direct feeding of the cooling media to the place which is to be cooled, permits operation with only relatively small amounts of cooling media which reduces the discharge problems. Intolerable heating of bone substance or tooth substance can also be avoided if work is done relatively quickly, namely if a relatively large quantity of such substance is removed per time unit. Rapid working with the previously used methods was difficult because of an insufficient cooling. Repeated pauses were necessary to prevent an excessive heating and to repeatedly cool a deep hole at short intervals due to the fact that cooling fluid was injected only after the tool was withdrawn.

In addition, the drilling or milling apparatus is not only usable in dentistry, but may be used wherever live bone is removed or severed. The severing of jaw bones, for example in prognathic operations, in jaw surgery and severing of head bones in neurosurgery, throat, nose and ear cases are a few examples. It is desired, and in many cases also an absolute condition for success, that the bone tissue does not suffer heat damages, because otherwise it is very difficult or not at all possible to heal implantations or severed bone. With the inventive apparatus, it is possible not to exceed the highest temperature of approximately 50° C., which the tooth or bone tissue will permit, not even during quick working.

SUMMARY OF THE INVENTION

In a preferred embodiment of the invention, the conduit is a stationary small tube which extends into the longitudinal channel. This has the advantage that the cooling fluid does not contact the driving members of the apparatus, for example a miter gear or a bearing for the drive shaft, which avoids corrosion of such parts. Corrosion danger exists both in using water and also in particular in using a saline solution as a cooling media. However, the invention is not limited to the use of a stationary small tube. The feed can also be accomplished through the chamber in the handle in which the drive shaft is supported. In this case the chamber is flooded by the cooling media and the cooling media passes from same directly through the longitudinal channel to the tip of the tool. This construction is primarily advantageous when the handle is a handle piece which prevents such an arrangement of the drive as to permit a small tube to be introduced in an extension of the drill. By choosing suitable materials which do not corrode, it is possible to flood the drive chamber with cooling fluid. The small tube extends through a seal arranged in a longitudinal channel, which seal closely contacts the outside of the small tube and closes the front part of the longitudinal channel at the back thereof. This prevents cooling fluid from reaching into the drive chamber.

According to a further development of the invention a space which is used as a return channel is provided between the exterior wall of the small tube and the wall, which space opens outwardly through a lateral outlet opening. Flushing nozzles can thus be associated with the outlet opening, from which flushing nozzles flushing jets can be directed toward the outlet opening exit. In such an apparatus, it is possible to reliably remove cooling fluid, and also to remove the substance being worked, from a deep drilled hole. This again is advantageous for an uninterrupted rapid operation, because interruptions of the milling or drilling operation for the purpose of flushing of removed substance are now unnecessary.

According to a further development of the invention, the small tube is composed of a pair of series connected small tubes, the end most one of which is smaller in diameter than the next adjacent tube. The smaller diameter tube engages the seal and serves to locate the series connected tube in coaxial relation to the drive shaft for the tool. In addition, the relative movement between the seal and the smaller diameter tube is very small and deterioration of the seal is thereby minimized.

The apparatus can additionally, to the described inventive cooling device, be equipped with a conventional cooling device which feeds cooling fluid from outside to the working end of the tool.

BRIEF DESCRIPTION OF THE DRAWINGS

In the drawings

FIG. 1 is a cross-sectional view of an apparatus according to a first embodiment of the invention, in which the tool is a drill, wherein the condition during the insertion of a drill is illustrated;

FIG. 2 is a cross-sectional view of a further embodiment of the invention in which a guide part is arranged between the tool and an elbow;

FIG. 3 is a longitudinal cross-sectional view of another embodiment of a dental hand piece taken along the line III—III of FIG. 4; and FIG. 4 is a cross-sectional view taken along the line III—III in FIG. 3.

DETAILED DESCRIPTION

The main parts of the apparatus according to FIG. 1 are an elbow 1, a drill or tool holder 2 and a small tube 3 for feeding of cooling fluid.

The elbow 1 includes a conventional handle 4, in which a shaft 5 is rotatably supported and a head 6 having a guide bore therein. A hollow shaft 8 is rotatably supported is the guide bore 7, which hollow shaft carries a bevel gear 9 which meshes with a bevel gear 10 mounted on the shaft 5. A driving surface 11 is provided at the upper end of the hollow shaft 8.

A slide 12 is arranged on the head 6, which slide carries a lock 13.

The construction of an elbow as thus far described is already known. The new construction provides that in the slide 12 there is provided an upwardly open groove 14 into which a horizontal part 3a of the small tube 3 can be inserted. The groove 14 passes into an opening 15 through which a vertical zone 3b of the small tube 3 can be placed. On the other side of the opening 15 there is provided on the underside of the slide 12 an extension 14a of the groove 14 which, however, opens in the downward direction.

The drill or tool holder 2 has a shaft 16 with a central bore 17 therein. A driving surface 18 and a locking annular groove 19 for engagement with the lock 13 is provided at the upper end of the shaft in a conventional manner.

In the shaft 16 has an internally threaded recess 23 therein and the tool 20 is screwed thereto by means of a thread 21 and is fixed by means of a lock nut 22. A soft-elastic perforable seal 24 of rubber or plastic lies in the recess 23 between the base thereof and the end of the tool 20. A longitudinal channel 25 is also arranged in the working tool 20, which channel is in alignment with the channel 17 in the shaft 16. Cross bores 26 are arranged at the lower end of the drill 20, which cross bores terminate in the longitudinal channel 25.

For insertion of a drill, the slide 12 is placed in its retracted position (illustrated position) and the shaft of the drill is introduced into the guide bore 7 until the stop shoulder 27 rests against the lower end of the guide bore 7. The driving surface 18 on the shaft thus engages the driving surface 11 on the hollow shaft.

The part 3b of small tube 3 is now pushed from above through the seal 24 until the horizontal part 3a comes to rest against the bottom of the groove 14. The seal can be weakened at the point which must be perforated (not shown in the drawing). The locking slide 12 is now moved to the right, which causes the groove part 14a to be moved over the part of the small tube zone 3a which is adjacent the knee 28. The left end of the enlarged small tube part 3c thus enters into a groove enlargement 29. From the illustration, it is easily seen that after shifting of the slide to the right, the small tube is fixed in its axial direction.

In working with the apparatus, cooling fluid is fed through the small tube 3, which cooling fluid passes through the longitudinal channel 25, thence through the cross bores 26 to the working location. Penetration of the cooling fluid into the chamber 30 is prevented by the seal 24, by which the driving members contained in the chamber 30, particularly the bevel gears 10, 9, are protected against damaging influence from the cooling fluid, namely corrosion.

In the embodiment according to FIG. 2, the apparatus again has an elbow identified as a whole with reference number 31 and a working tool identified as a whole with reference numeral 32, which working tool is, however, in this case a milling tool. In addition to the exemplary embodiment of FIG. 1, there is here provided a guide part identified as a whole with reference numeral 33. The scale of FIG. 2 is smaller than the one of FIG. 1, in that the milling tool 32 is in reality substantially larger than the drill 20 in the embodiment of FIG. 1 but smaller than illustrated in the drawing.

The elbow 31 is only schematically illustrated in FIG. 2. It is constructed similar to the elbow of FIG. 1, in particular it contains also a bevel gear and drive shaft which is constructed as a hollow shaft and a guide tube. All of these parts are not shown in order to simplify the drawing.

The guide part 33 has a member 34 on which a guide tube 35 is secured. A recess 36 is provided in the member 34, which recess opens outwardly through an outlet opening 37. The member 34 has a spherical indentation 38 which fits onto the spherical surface 39 at the head of the elbow 31. In the zone of the shoulder of the spherical surface there are provided two parallel horizontal bores 40 which are laterally spaced from the longitudinal axis 41 of the head 6. FIG. 2 illustrates in cross section only one of these two bores. In the member 34, there are provided two corresponding bores 41 which are in alignment with the bores 40 when the guide part 33 is mounted on the head 6. A slide 42 can be placed through the bores 40, which slide has two parallel pins 43. From the drawing, it is clear that after the member 34 is mounted on the spherical surface 39, placement of the slide pins 43 through the bores 40, 41, will fix guide part 33 onto the head 6.

A conduit system 44 is mounted on the member 34 which conduit system has a supply main 45, flushing nozzles 46 and cooling nozzles 47 directed toward the recess 36.

A small tube 3' is also associated with the apparatus according to FIG. 2, which small tube is constructed substantially similarly to the small tube 3 of FIG. 1. The difference consists in that the vertical part 3b' is longer than the vertical part 3b of the small tube 3 of FIG. 1.

The milling tool 32 consists of three main parts, namely a first shaft 48 which fits into the elbow 31, a second shaft 49 which fits into the guide tube 35 and a milling head 50.

The first shaft 48 is similar to the shaft 16 of the drill of FIG. 1 so that it fits into the elbow 31 and can be coupled to its drive shaft 8 (not illustrated in FIG. 2). In place of a drill, the additional shaft 49 is screwed into said first shaft 48, which shaft 49 also holds a soft-elastic seal 51 corresponding to the seal 24 of FIG. 1. The shaft 49 is hollow and has only a relatively thin wall 54.

The milling head 50 is also hollow (cavity 60) and has only a thin wall 55. The upper part of the milling head has the same outside diameter as the shaft 49 and can be coupled to same in such a manner that nose-shaped projections 56 on the shaft 49 and 57 engage the milling head 50. At the lower part of the milling head there are provided working cutting edges 58. In the recesses between the cutting edges there are provided elongated windows 59 for cooling fluid to exit and boring dust and flushing liquid to enter. The windows 59 are sufficiently long that the part of the milling head which is provided with the cutting edges somewhat resembles a basket.

During assembly of the apparatus according to FIG. 2, the guide part 33 is first mounted onto the elbow 31 and is fixed by means of the slide 42 on the elbow 31. Prior to the insertion of the tool into the guide part 33, the milling head 50 is coupled with the shaft 49. Thereafter the thus assembled unit is placed into the guide part 33 and the shaft 48 guided into the elbow 31. When the shaft 49 and the upper part of the milling head 50 lie in the guide tube 35, they are undetachably held together, because the guide in the tube 35 prevents a lateral escape and hence uncoupling of the milling head 50 with respect to the shaft 49.

As is described in connection with FIG. 1, the small tube 3' is now inserted, by which it pierces the soft-elastic seal 51 and its front end reaches closes to the lower end of the milling head cavity 60. The locking of the drill and of the small tube is now effected by shifting the slide 12, as already described in connection with FIG. 1. In using the apparatus, cooling fluid is conducted both through the small tube 3' and also through the conduit system 44. This cooling fluid is conducted into the front end of the cavity 60 and exits from the openings 59, whereby cooling fluid is available directly at the working location. The cooling fluid also enters again into the cavity 60 through the openings 59, whereby boring dust is washed into the cavity 60. Since the entire cross section of the opening 59 is relatively large, it is assured that the cooling fluid, which is supplied under pressure, will reach the working location through the small tube 3' which extends into the zone of the openings 59.

The mixture of boring dust and cooling fluid rises upwardly in the area 60 and exits through the spaces 61 between a flange 62 on the shaft 48 and the shaft 49. This space lies in the assembled apparatus at the level of the cutout 36. The flushing nozzles 46 provide a flow which assists the exiting of the fluid through the opening 37.

During the operation it is possible additionally to flush out cooling fluid through the cooling nozzles 47.

ALTERNATE CONSTRUCTION

The main parts of the apparatus are a hand piece 71, a drill 72 and a small tube 73 for feeding of cooling fluid.

The hand piece 71 has a bearing member 74, onto which can be screwed a sleeve 76. A thread 77 is for this purpose provided on the bearing member 74. A shoulder 78 is provided on the upper end of the thread 77 on the bearing member, against which shoulder the sleeve 76 can be tightened.

A shaft 75 is supported in the bearing member, which has a carrier slot 79 in its upper end and to which can be coupled a drive motor. The lower end of the shaft 75 has teeth thereon defining a crown gear 80 which engage a large gear 81. The gear 81 is (here compare also FIG. 2) fixedly connected to a gear shaft 82 and is rotatable therewith. A small gear 83 is also fixed to the shaft 82 and rotatable therewith. The shaft 82 is supported in an opening through the bearing member 74.

A hollow sleeve 84 is supported in the sleeve 76, which hollow shaft has a crown gear 85 at its upper end. The upper end of the hollow shaft 84 is supported in a bearing 89 and the lower end in a bearing 91. In the assembled condition of the hand piece, the small gear 83 engages the crown gear 85. From a study of the drawing, it will be clear that by mating of the small crown gear 80 on the shaft 75 with the large gear 81, a first reduction is defined and by mating of the small gear 83 with the large crown gear 85 a second reduction step is defined so that the hollow shaft 84 runs substantially slower than the shaft 75.

The small tube 73 has a lower section 92 having a small diameter, for example an outer diameter of 0.6 to 0.7 mm., which transfers into an upper straight section 97 of larger diameter. The outer diameter of the section 97 may for example be 1.5 mm. The section 97 transfers through an obtuse angle into a sloped section 98 and same in turn transfers through an obtuse angle into an axially parallel section 99. The axially parallel section 99 transfers through a right angle into a short section 100, which extends perpendicularly with respect to the axis 101 of the hand piece. The section 100 is followed by a last section 102, which is inclined slightly away from the wall of the hand piece. A thin plastic hose is placed on the section 102, through which hose cooling fluid is supplied.

As is shown in the cross-sectional view of FIG. 2, the sloped section 98 is received in a groove 103 in the bearing member 74. The groove bottom 104 extends from the center of the bearing member to approximately its periphery and transfers into an axially parallel section 104a, which finally ends in a section 104b. The axial spacing of the section 104b from the shoulder 78 equals the diameter of the small tube 73. The groove 103 is designed such that an interference with the gears 81, 83 and their supporting shaft 72 cannot occur.

The drill 72 has a shaft or tool holder 86 with a central bore 87 therethrough. The drill 72 also has an outer driving surface 88 and an annular groove 40. The actual tool 90 is secured to the shaft 86, which tool in turn has a central longitudinally extending channel 95 and cross holes 96 which communicate with the interior of the channel 95 and terminate toward the outside of the drill, preferably within the flutes of the tool part 90. A soft elastic seat 94 is also provided in the drill, which seal is made of rubber or plastic and is clamped sealingly between the upper end of the tool 90 and the lower end of the shaft 86. A projection 93 is provided in the interior of the hollow shaft 84, which projection is used to take along the drill 72. When the drill is inserted, the driving surface 88 rests on the projection 23.

FIG. 3 illustrates the small tube 73 in mounted condition. It is held in its position by engagement with the sloped section 98 in the groove 103 and by fixing the short section 100 between the upper edge of the sleeve 76 and the groove bottom section 104b to prevent an axial shifting thereof. When the drill 72 is inserted, the lower section 92 of the tube 3 penetrates through the soft elastic seal 94 and projects into the longitudinal channel 95 of the tool 90. The small tube is thus fixed in radial direction, so that its section 97, which is relatively rigid, cannot slide along the wall of the cavity 105. Due to the very small diameter of the lower section 92, one obtains a very good seal on the periphery of the small tube and even at high rotational speed only small peripheral speeds at the sealing point. The transition from the stationary liquid conduit (small tube 73) into the rotating tool has been solved in a manner by which sealing problems are substantially reduced.

A sliding button 106 is provided on the outside of the sleeve 76, which button is used to operate a locking mechanism for the tool, which locking mechanism is not illustrated in the drawing. Balls are received in the groove 110 on the shaft 86 of the drill 72 through the operation of the locking mechanism.

The small tube 73 can quickly be removed, namely by unscrewing the sleeve 76 and removing the small tube laterally from the groove 103. The sleeve 76 can then again be screwed on and can be equipped with normal tools, namely those which do not have a longitudinal channel. This assures the universal use of the hand piece.

A special embodiment has been described in connection with the drawings. Of course, the path of the small tube may differ substantially from the described path, if this is necessary to adjust to the structural conditions of the hand piece.

Although particular preferred embodiments of the invention have been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a hand held apparatus including a handle having driving shaft means rotatably supported thereon and tool means rotatably driven by said driving shaft means, said driving shaft means including means thereon defining a passageway extending coaxially therethrough, the improvement comprising tube means extending through said passageway means for carrying a fluid therethrough, said tube means being smaller in size than said passageway means to define a clearance space therebetween, said tool means having a work end and means defining a longitudinal channel therein communicating with said work end;
   resilient seal means separate from said tool means at the end of said longitudinal channel means remote from said work end; and
   coupling means for coupling said tool means to said driving shaft means, said tube means extending into said longitudinal passageway means, the exterior of said tube means and the end of said tool means remote from said work end being tightly engaged with said resilient seal means to seal said longitudinal channel means adjacent the end thereof remote from said working end of said tool means from said passageway means in said driving shaft means.

2. The improved apparatus according to claim 1, wherein said handle includes means defining an elbow and slide means for fixing said tool means to said handle, said slide means having groove means therein, said tube means being received in said groove means in said slide means and includes a 90° bend therein.

3. The improved apparatus according to claim 1, wherein said guide part means includes an exterior cooling device for feeding cooling fluid to the external surface of said tool means.

4. The improved apparatus according to claim 1, wherein said tube means comprises plural series connected small tubes, the endmost one of said small tubes at the free end of said plural tubes being smaller in diameter than the next adjacent tube.

5. The improved apparatus according to claim 4, wherein the endmost one of said tubes extends through said seal means.

6. The improved apparatus according to claim 5, wherein the smaller diameter tube has an outer diameter in the range of 0.6 to 0.7 mm. and the next adjacent tube has an outer diameter of 1.5 mm., and the seal is located between the tool and a tool holder.

7. The improved apparatus according to claim 4, wherein said next adjacent tube extends without contact through said driving shaft means and said seal means holds the end of said next adjacent tube adjacent tube adjacent said tool means concentric with respect to said driving shaft means.

8. The improved apparatus according to claim 4, wherein said handle has reduction gear means therein, the driving side of said reduction gear means being coupled to said driving shaft means which includes a driven shaft, and wherein said tube means extends only through said driven shaft and out through an opening in the side of said handle adjacent the rear end of said driven shaft.

9. The improved apparatus according to claim 8, wherein said reduction gear means includes a bearing member having means defining a groove therein;
   wherein said next adjacent tube is received in said groove means, the bottom of said groove means extending at an acute angle with respect to the longitudinal axis of said handle and in a radial plane such that radially outermost portion of said groove means lies closer to a rear end of said handle than its radially innermost portion.

10. The improved apparatus according to claim 9, wherein said next adjacent tube has a short section extending perpendicularly with respect to said handle, which section extends out through a sleeve member mounted on said handle and engages an abutment surface for an axial fixation in direction of said rear end of said handle and engages an edge of said sleeve member for the axial fixation in the opposite direction toward said tool, said sleeve member and said bearing member having cooperating threads thereon for effecting a releasable securement of said sleeve member to said bearing member.

11. The improved apparatus according to claim 1, wherein said handle includes a hollow guide part means, wherein said tool means includes a guide tube and a tool, said guide tube being received in said guide part means and wherein said resilient seal means is located between said tool and said guide tube.

12. The improved apparatus according to claim 11, wherein said passageway in said driving shaft means is defined by the spacing between the outside wall of said tube means and the interior wall of said guide part means.

13. The improved apparatus according to claim 11, wherein said guide tube is connected to said driving shaft means.

14. The improved apparatus according to claim 11, wherein said guide part means is connected to said handle by a lock which includes at least one pin which is received in aligned bores in said guide part means and in said handle.

15. The improved apparatus according to claim 12, including flushing nozzles located adjacent said passageway and directed toward said passageway.

16. The improved apparatus according to claim 14, wherein said handle and said guide part means each have a pair of parallel and axially aligned bores therein for receiving a pair of lock pins therein, said pair of bores being located on diametrically opposed sides of said hollow guide part means.

17. The improved apparatus according to claim 6, wherein said tool means includes a tool holder and a tool connected to said tool holder; and wherein said seal means is located between said tool and said tool holder.

18. The improved apparatus according to claim 8, wherein said reduction gear means is driven by a drive shaft rotatably supported in said handle and axially aligned with said driven shaft.

* * * * *

UNITED STATES PATENT AND TRADEMARK OFFICE
CERTIFICATE OF CORRECTION

PATENT NO. : 4 021 920
DATED : May 10, 1977
INVENTOR(S) : Horst Kirschner and Wolfgang Meyer It is certified that error appears in the above-identified patent and that said Letters Patent are hereby corrected as shown below:

Column 8, line 42; change to read as follows: ---tube has an outer diameter of 1.5 mm.---.

line 43; delete in its entirety.

Column 8, line 46; after second occurrence of "said" insert ---resilient---.

Column 8, line 47; after "adjacent" delete ---tube adjacent---.

Column 8, line 65; after "that" insert ---the---.

Column 10, line 21; after first occurrence of "said" insert ---resilient---.

Signed and Sealed this

Twenty-second Day of November 1977

[SEAL]

Attest:

RUTH C. MASON
Attesting Officer

LUTRELLE F. PARKER
Acting Commissioner of Patents and Trademarks